(12) United States Patent
Wang et al.

(10) Patent No.: US 12,076,491 B2
(45) Date of Patent: Sep. 3, 2024

(54) ANESTHETIC EVAPORATOR AND ANESTHESIA MACHINE

(71) Applicants: SHENZHEN MINDRAY BIO-MEDICAL ELECTRONICS CO., LTD., Shenzhen (CN); SHENZHEN MINDRAY SCIENTIFIC CO., LTD., Shenzhen (CN)

(72) Inventors: Congquan Wang, Shenzhen (CN); Shiming Ai, Shenzhen (CN); Peitao Chen, Shenzhen (CN); Xuetao Wu, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 1172 days.

(21) Appl. No.: 16/757,368

(22) PCT Filed: Oct. 20, 2017

(86) PCT No.: PCT/CN2017/107130
§ 371 (c)(1),
(2) Date: Oct. 13, 2020

(87) PCT Pub. No.: WO2019/075753
PCT Pub. Date: Apr. 25, 2019

(65) Prior Publication Data
US 2021/0016048 A1    Jan. 21, 2021

(51) Int. Cl.
*A61M 16/18* (2006.01)
*A61M 16/20* (2006.01)
*A61M 16/00* (2006.01)

(52) U.S. Cl.
CPC ........ *A61M 16/183* (2013.01); *A61M 16/208* (2013.01); *A61M 2016/0027* (2013.01); *A61M 2202/0241* (2013.01)

(58) Field of Classification Search
CPC .............. A61M 16/00; A61M 16/0003; A61M 16/0087; A61M 16/009; A61M 16/01;
(Continued)

(56) References Cited

U.S. PATENT DOCUMENTS

| | | |
|---|---|---|
| 5,799,711 A | 9/1998 | Heinonen et al. |
| 5,810,001 A | 9/1998 | Genga et al. |

(Continued)

FOREIGN PATENT DOCUMENTS

| | | |
|---|---|---|
| CN | 101537220 A | 9/2009 |
| CN | 102029000 A | 4/2011 |

(Continued)

OTHER PUBLICATIONS

International Search Report issued in corresponding International Application No. PCT/CN2017/107130, mailed Jul. 18, 2018, 4 pages.
(Continued)

*Primary Examiner* — Colin W Stuart
(74) *Attorney, Agent, or Firm* — BAYES PLLC

(57) ABSTRACT

An anesthetic evaporator is provided. The anesthetic evaporator includes a housing, an anesthetic agent storage tank, a cover, a mechanical pressure relief assembly connected with the anesthetic agent storage tank, and a linkage mechanism. The mechanical pressure relief assembly is provided with a first state in which a pressure within the anesthetic agent storage tank is maintained and a second state in which a pressure within the anesthetic agent storage tank is released. When adding an anesthetic agent, an operation action on the anesthetic evaporator drives the linkage mechanism, and the
(Continued)

linkage mechanism drives the mechanical pressure relief assembly to be switched from the first state to the second state.

19 Claims, 6 Drawing Sheets

(58) Field of Classification Search
CPC .... A61M 16/10; A61M 16/104; A61M 16/14; A61M 16/18; A61M 16/183; A61M 16/186; A61M 16/20; A61M 16/208; A61M 2016/0027; A61M 2202/0241; A61M 2209/04; A61M 2209/045
See application file for complete search history.

(56) References Cited

U.S. PATENT DOCUMENTS

| | | | |
|---|---|---|---|
| 6,585,016 B1* | 7/2003 | Falligant | A61M 16/183 141/354 |
| 6,878,133 B2* | 4/2005 | Ahlmen | A61M 16/183 604/246 |
| 7,886,780 B2 | 2/2011 | Falligant et al. | |
| 2010/0269820 A1 | 10/2010 | Danielsen et al. | |
| 2010/0294276 A1* | 11/2010 | Rindy | A61M 16/183 141/346 |

FOREIGN PATENT DOCUMENTS

| | | |
|---|---|---|
| CN | 103133865 A | 6/2013 |
| CN | 204337469 U | 5/2015 |
| CN | 206534970 U | 10/2017 |
| DE | 4108383 A1 | 9/1992 |
| WO | 2008151667 A1 | 12/2008 |

OTHER PUBLICATIONS

1 European Search Report issued in related European Application No. 17929005.1, mailed Oct. 8, 2020, 7 pages.

* cited by examiner

ANESTHETIC EVAPORATOR AND ANESTHESIA MACHINE

TECHNICAL FIELD

This disclosure relates to the field of medical apparatuses, and in particular to an anesthetic evaporator and an anesthesia machine using the same.

BACKGROUND

During the operation of an injection anesthetic evaporator, a driving gas needs to be introduced into an anesthetic agent storage chamber, so that a certain pressure is applied to an anesthetic agent stored in the anesthetic agent storage chamber to make the anesthetic agent be sprayed out of a nozzle in a mist form, and then enter the body of a patient after being mixed with air and oxygen. During the operation of the above-mentioned injection anesthetic evaporator, when it is needed to add the anesthetic agent to the anesthetic agent storage chamber, the pressure within the anesthetic agent storage chamber should be released first, otherwise when a tank containing the anesthetic agent is inserted into an anesthetic agent adding port, a large amount of anesthetic agent will be sprayed out from the anesthetic agent adding port, causing harm to an operator. One of the technical solutions to solve this problem is to provide a sensor on an anesthetic agent adding cover, where the sensor is used to detect a cover opening action, and thus a control signal is sent to a pressure relief electromagnetic valve to realize automatic pressure relief during a cover opening process. However, this solution requires the sensor and the pressure relief electromagnetic valve to cooperate with each other to realize the automatic pressure relief, and when the sensor or the pressure relief electromagnetic valve fails, i.e. does not work normally, the safety and reliability will become low.

SUMMARY OF THIS DISCLOSURE

Based on this, it is necessary to provide an anesthetic evaporator aiming at the problem of low safety and reliability during the process of anesthetic agent adding and pressure relief.

This disclosure can provide an anesthetic evaporator that may include a housing, an anesthetic agent storage tank and a cover that is moveably connected with the housing, where the anesthetic agent storage tank can be provided with an anesthetic agent adding barrel arranged corresponding to the cover. The anesthetic evaporator may further include a mechanical pressure relief assembly and a linkage mechanism. The mechanical pressure relief assembly is connected with the anesthetic agent storage tank, and the mechanical pressure relief assembly may have a first state in which the pressure within the anesthetic agent storage tank is maintained and a second state in which the pressure within the anesthetic agent storage tank is released. When adding an anesthetic agent, an operation action on the anesthetic evaporator may drive the linkage mechanism, and the linkage mechanism may drive the mechanical pressure relief assembly to be switched from the first state to the second state.

In an embodiment, a first end of the linkage mechanism may be connected with the cover, a second end thereof may be connected with the mechanical pressure relief assembly, and the operation action on the anesthetic evaporator may be a cover opening action.

In an embodiment, the operation action on the anesthetic evaporator may be an action to push an anesthetic agent adding container into the anesthetic agent adding barrel.

In an embodiment, a first end of the linkage mechanism may extend into the anesthetic agent adding barrel, and a second end thereof may be connected to the mechanical pressure relief assembly.

In an embodiment, the mechanical pressure relief assembly may include a main body, a first pipe, a second pipe, a third pipe, and a valve stem assembly. A first end of the first pipe may be connected with the main body, and a second end thereof may be connected with a driving gas source; a first end of the second pipe may be connected with the main body, and a second end thereof may be connected with an exhaust gas treatment system; a first end of the third pipe may be connected to the main body, and a second end thereof may be in communication with the anesthetic agent storage tank; and the linkage mechanism may be connected with the valve stem assembly.

In an embodiment, when the valve stem assembly is in a first position, the first pipe can be in communication with the third pipe, and the mechanical pressure relief assembly can be in the first state; and when the anesthetic agent is added, the corresponding operation action is performed on the anesthetic evaporator, the linkage mechanism may be driven to push the valve stem assembly to move to a second position, such that the third pipe becomes in communication with the second pipe, and the mechanical pressure relief assembly can be in the second state.

In an embodiment, the valve stem assembly may include a valve stem and an elastic member, where a first end of the elastic member may be connected with a side wall of the main body, and a second end thereof may be connected with the valve stem.

In an embodiment, the anesthetic evaporator may further include a pressure sensor and a switch valve provided on the third pipe, and the pressure sensor may be located between the switch valve and the main body.

In an embodiment, the linkage mechanism may be a cam mechanism, where a first end of the cam mechanism may be fixedly connected with the cover, and a second end thereof is slidably connected to the valve stem assembly.

In an embodiment, the linkage mechanism may be a connecting rod mechanism, where a first end of the connecting rod mechanism is rotatably connected with the cover, and a second end thereof is rotatably connected with the valve stem assembly.

In an embodiment, a side wall of the anesthetic agent adding barrel may be provided with a sliding groove, the anesthetic agent adding container may be formed with a mating portion, and when the linkage mechanism extends into the anesthetic agent adding barrel through the sliding groove, the mating portion may abut against the first end of the linkage mechanism.

In an embodiment, the linkage mechanism may include a connection body and a transmission body which two are rotatably connected, one end of the connection body that is remote from the transmission body may be connected with the mechanical pressure relief assembly, and an end of the transmission body may extend into the anesthetic agent adding barrel.

In an embodiment, the anesthetic evaporator may further include a liquidometer for detecting a liquid level within the anesthetic agent storage tank, and/or, the anesthetic evaporator may further include a sealed valve accommodated in the anesthetic agent adding barrel.

In an embodiment, the anesthetic evaporator may further include a pipeline, a nozzle and an evaporation chamber which are in communication with the anesthetic agent storage tank, where a first end of the pipeline may be arranged at a bottom of the anesthetic agent storage tank, a second end thereof may be connected with the nozzle, and the evaporation chamber may be provided with a gas inlet and a gas outlet.

Also disclosed is an anesthesia machine, comprising the above-mentioned anesthetic evaporator.

In the above-mentioned anesthetic evaporator, the linkage mechanism and the mechanical pressure relief assembly are provided to cooperate with each other, such that the operation action on the anesthetic evaporator in the anesthetic agent adding process can act as the driving force of the linkage mechanism, thereby controlling the mechanical pressure relief assembly to be switched from the first state to the second state to prevent the driving gas from entering the anesthetic agent storage tank, and at the same time, the high-pressure driving gas in the anesthetic agent storage tank is discharged outward such that the pressure within the anesthetic agent storage tank is reduced during the anesthetic agent adding by realizing the pressure relief in a mechanical manner. This mechanical pressure relief method makes the safety and reliability of the anesthetic evaporator be higher.

BRIEF DESCRIPTION OF THE DRAWINGS

In order to more clearly illustrate technical solutions in the embodiments of this disclosure or in the prior art, a brief introduction to the drawings required for the description of the embodiments or the prior art will be provided below. Obviously, the drawings in the following description are only some of the embodiments of this disclosure, and those of ordinary skilled persons in the art would also be able to obtain other drawings from these drawings without involving any inventive effort.

DETAILED DESCRIPTION

To make the objectives, technical solutions and advantages of this disclosure be more clearly, this disclosure will be further described below in detail in conjunction with the accompanying drawings and the embodiments. It should be understood that the specific implementations described herein are only used to explain this disclosure and do not limit the protection scope of this disclosure.

Figure 1:
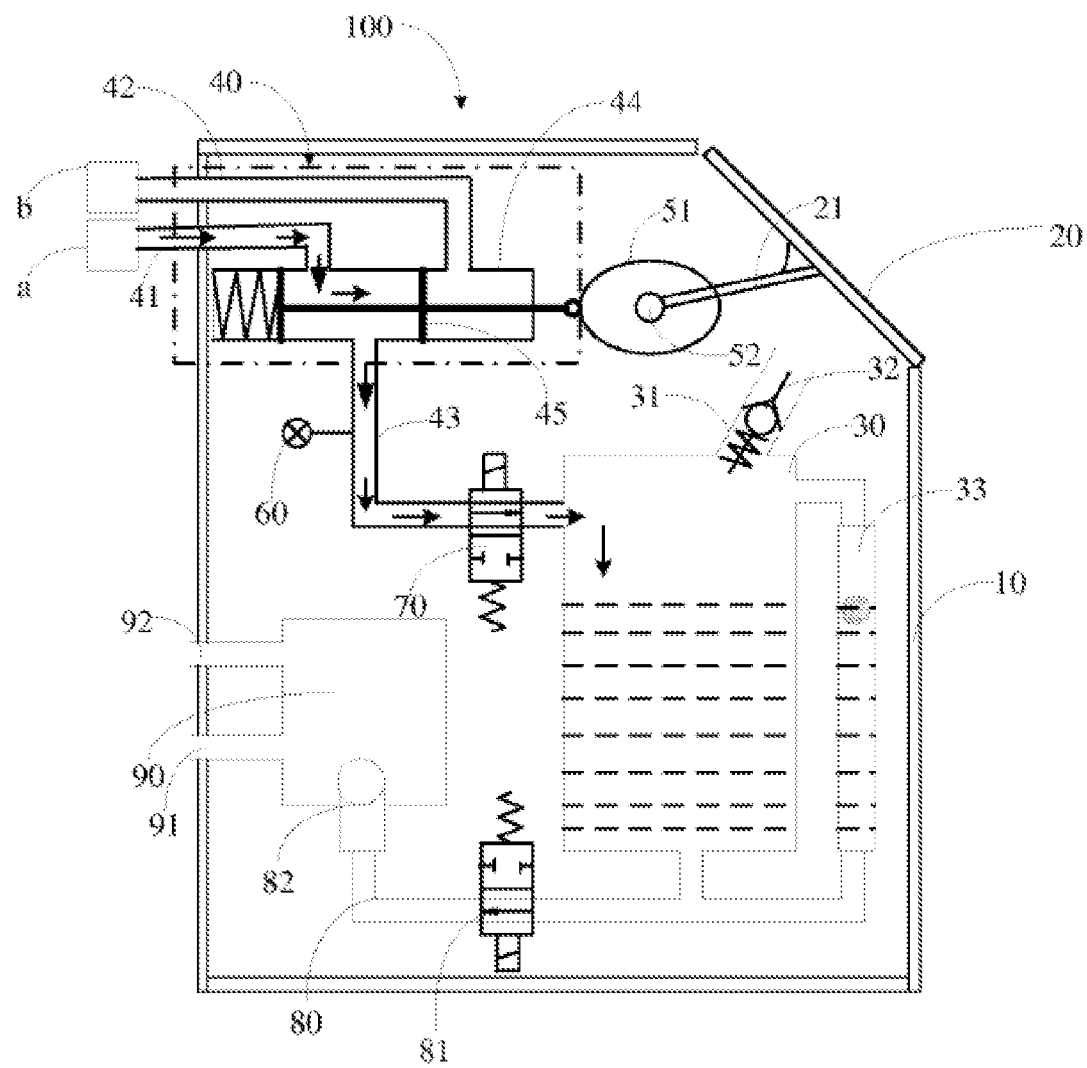
FIG. 1 is a schematic structural diagram of a mechanical pressure relief assembly of an anesthetic evaporator in an embodiment, where the mechanical pressure relief assembly is in a first state.
Figure 2:
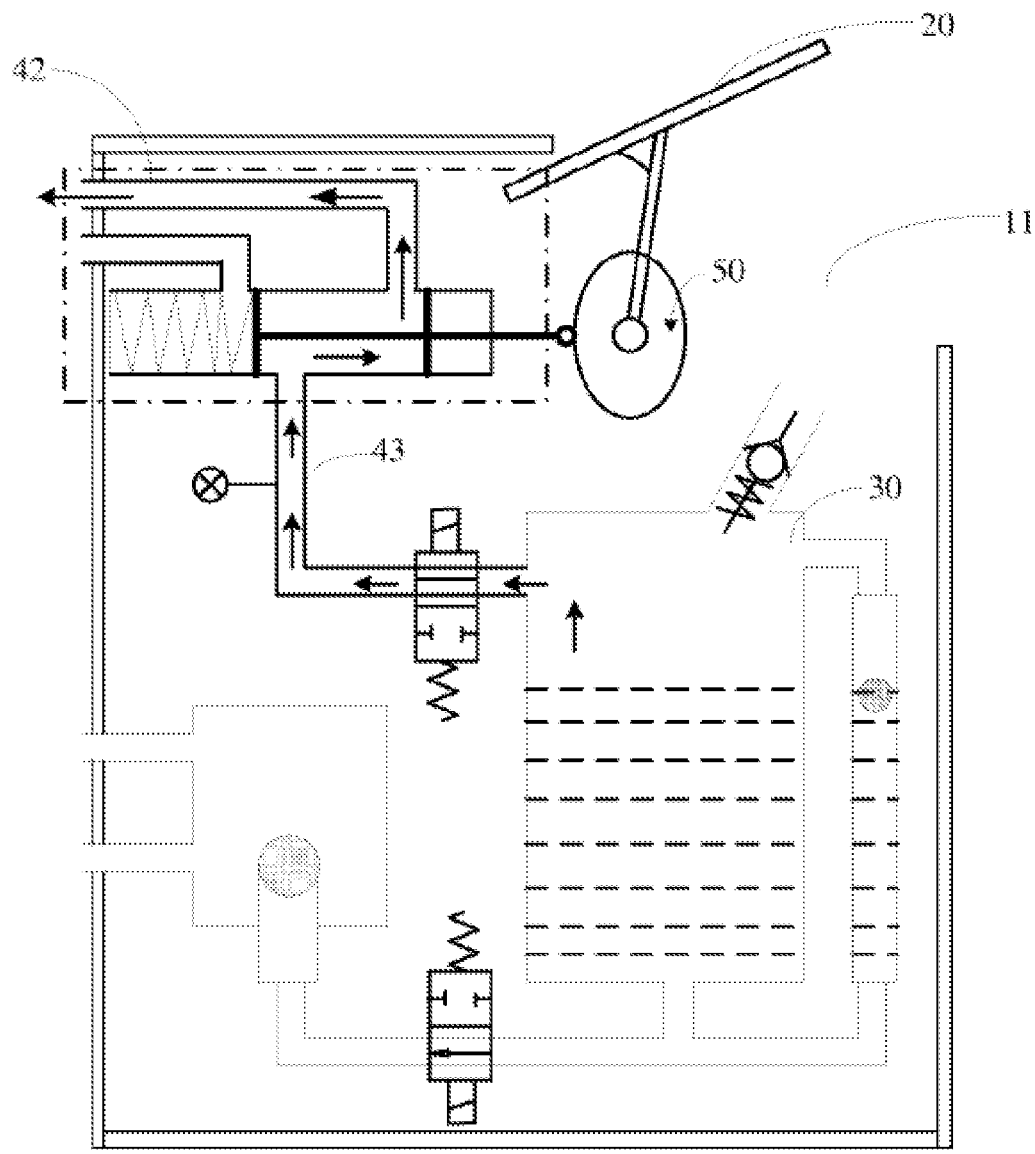
FIG. 2 is a schematic structural diagram of the mechanical pressure relief assembly of the anesthetic evaporator in FIG. 1 in a second state.

Referring to FIG. 1 and FIG. 2, an anesthetic evaporator 100 may include a housing 10, a cover 20, a linkage mechanism 50, a mechanical pressure relief assembly 40 and an anesthetic agent storage tank 30. The housing 10 may be provided with an opening 11, the cover 20 is rotatably connected with the opening 11 of the housing 10, and the anesthetic agent storage tank 30, the mechanical pressure relief assembly 40 and the linkage mechanism 50 can be accommodated in a space enclosed by the housing 10 and the cover 20. The mechanical pressure relief assembly 40 may be in communication with an external driving gas source and the anesthetic agent storage tank 30, respectively, and may also be connected with the linkage mechanism 50. The mechanical pressure relief assembly 40 can be provided with a first state in which the pressure within the anesthetic agent storage tank 30 is maintained and a second state in which the pressure within the anesthetic agent storage tank 30 is released. Specifically, releasing the pressure within the anesthetic agent storage tank 30 may mean that gas in the anesthetic agent storage tank 30 is discharged, so that an intensity of pressure within the anesthetic agent storage tank 30 can be kept at a low value. An operation action operated on the anesthetic evaporator 100 during an anesthetic agent adding process may act as a driving force of the linkage mechanism 50, such that the mechanical pressure relief assembly 40 can be switched from the first state to the second state.

In a first embodiment, referring to FIG. 1 and FIG. 2, the linkage mechanism 50 may be a cam mechanism, where a first end of the cam mechanism may be connected with the cover 20, and a second end thereof may be connected with a valve stem assembly 45 of the mechanical pressure relief assembly 40. When an anesthetic agent needs to be added, during an opening process of the cover 20, the cam mechanism may be driven to rotate, and then the valve stem assembly 45 may be pushed to move, so that the mechanical pressure relief assembly 40 is switched from the first state to the second state. Since the cam mechanism is connected with the cover 20, the cam mechanism is driven to move during the process of opening the cover 20 to realize the mechanical pressure relief, thus achieving higher safety and reliability of the anesthetic evaporator 100.

Specifically, the cam mechanism may include a cam 51 and a rotation shaft 52, where the cam 51 may be fixed to the rotation shaft 52, a tail end of the valve stem assembly 45 may be slidably connected with an edge of the cam 51, and the rotation shaft 52 may be rotatably connected with the housing 10. A connection rod 21 may be fixedly provided on the cover 20, where the connection rod 21 may be fixedly connected with the rotation shaft 52. The mechanical pressure relief assembly 40 may include a main body 44, a first pipe 41, a second pipe 42, a third pipe 43 and the valve stem assembly 45. The first pipe 41, the second pipe 42 and the third pipe 43 may all be in communication with the main body 44. The third pipe 43 may be in communication with the anesthetic agent storage tank 30. The valve stem assembly 45 may be partially accommodated in the main body 44, and a first end of the valve stem assembly 45 may be connected with an inner wall of the main body 44, and a second end (i.e., the tail end) thereof may be connected with the linkage mechanism 50. Specifically, when the linkage mechanism is the cam mechanism, the second end of the valve stem assembly 45 may be slidably connected with the edge of the cam 51. When the cover 20 is opened, the cam 51 can be driven by the connection rod 21 to rotate relative to the housing 10, thereby driving the valve stem assembly 45 to move.

The first pipe 41 may be connected with the driving gas source a, and the second pipe 42 may be connected with an exhaust gas treatment system b.

The anesthetic agent storage tank 30 may be connected with the mechanical pressure relief assembly 40, and specifically, connected to the third pipe 43 of the mechanical pressure relief assembly 40. The anesthetic agent storage tank 30 may contain the anesthetic agent, where a liquid level of the anesthetic agent is lower than a height of the connection between the mechanical pressure relief assembly 40 and the anesthetic agent storage tank 30, which can prevent the anesthetic agent from entering the mechanical pressure relief assembly 40 from the anesthetic agent storage tank 30.

An anesthetic agent adding barrel 31 may be provided at the top of the anesthetic agent storage tank 30, and the anesthetic agent adding barrel 31 can be arranged opposite the cover 20. When the cover 20 rotates relative to the housing 10 to open the opening 11 of the housing 10, the anesthetic agent adding barrel 31 may be exposed from the opening 11, which is convenient for an operator to perform an anesthetic agent adding operation to the anesthetic agent storage tank 30 via the anesthetic agent adding barrel 31. A sealed valve 32 may be provided in the anesthetic agent adding barrel 31 to seal the anesthetic agent storage tank 30. In an embodiment, the sealed valve 32 is a one-way valve. The sealed valve 32 may be provided to allow the anesthetic agent to enter the anesthetic agent storage tank 30 from the anesthetic agent adding barrel 31, and not allow the anesthetic agent to flow out of the anesthetic agent adding barrel 31 from the anesthetic agent storage tank 30.

The anesthetic agent storage tank 30 is also provided with a liquidometer 33 for displaying the liquid level of the anesthetic agent.

Referring to FIG. 1, when the anesthetic evaporator 100 works normally and when no anesthetic agent adding operation is performed, the valve stem assembly 45 is in a first position, the mechanical pressure relief assembly 40 is in the first state, the first pipe 41 is in communication with the third pipe 43, a driving gas is continuously introduced into the anesthetic agent storage tank 30 via the first pipe 41 and the third pipe 43 to maintain a high pressure state within the anesthetic agent storage tank 30, so that the anesthetic agent is in a mist form when sprayed out via a nozzle 82 in communication with the anesthetic agent storage tank 30. Referring to FIG. 2, when the anesthetic agent adding operation is required and when the cover 20 is opened, the linkage mechanism 50 is driven to move, the linkage mechanism 50 pushes the valve stem assembly 45 to move to a second position, the mechanical pressure relief assembly 40 becomes the second state, the third pipe 43 is in communication with the second pipe 42, the driving gas stops entering the anesthetic agent storage tank 30, and at the same time, the driving gas already within the anesthetic agent storage tank 30 is discharged via the third pipe 43 and the second pipe 42, thereby realizing pressure relief of the anesthetic agent storage tank 30.

Figure 4:
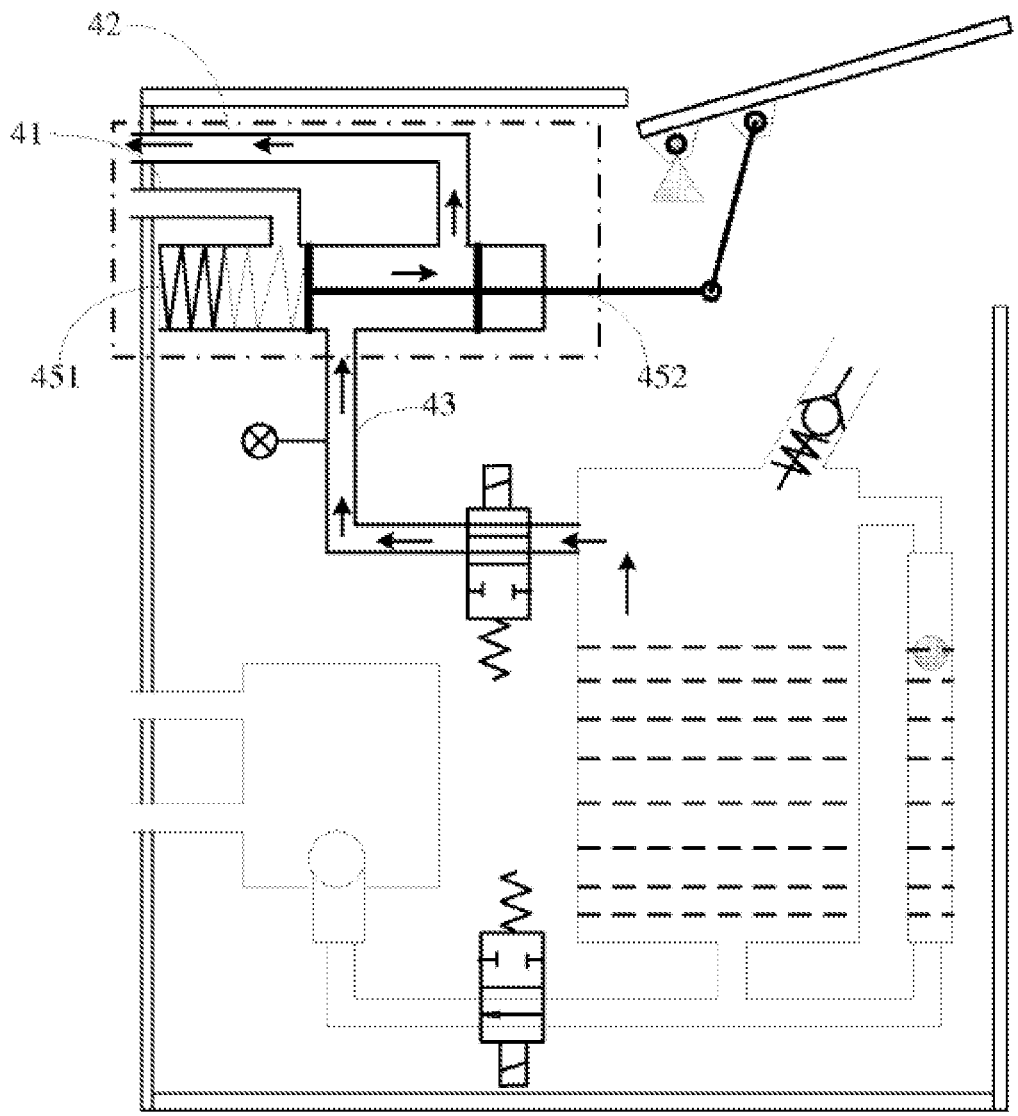
FIG. 4 is a schematic structural diagram of the mechanical pressure relief assembly of the anesthetic evaporator in FIG. 3 in a second state.

Referring to FIG. 4, the valve stem assembly 45 may include an elastic member 451 and a valve stem 452, where a first end of the elastic member 451 may be fixed to the valve stem 452, and a second end thereof may be fixed on a side wall of the main body 44.

Referring to FIG. 1 and FIG. 2, the anesthetic evaporator 100 may further include a pressure sensor 60 and a switch valve 70 provided on the third pipe 43, and the switch valve 70 may be arranged near the anesthetic agent storage tank 30. When the anesthetic evaporator 100 is in a working state and when anesthetic agent adding is required, by the cooperation of the linkage mechanism 50 and the mechanical pressure relief assembly 40, the mechanical pressure relief assembly 40 can be switched from the first state to the second state, so that the pressure within the anesthetic agent storage tank 30 decreases, and the anesthetic agent storage tank 30 is in communication with the third pipe 43. When the pressure sensor 60 provided on the third pipe 43 detects that the driving gas pressure within the anesthetic agent storage tank 30 is lower to a preset value, the switch valve 70 is controlled to be closed, thereby preventing the driving gas from being continuously discharged, and reducing the loss of the anesthetic agent. After the anesthetic agent adding is completed, the valve stem assembly 45 is moved from the second position to the first position under the push of the linkage mechanism 50, the first pipe 41 becomes in communication with the third pipe 43, and the driving gas enters the third pipe 43 via the first pipe 41. When the pressure sensor 60 detects that the driving gas pressure within the third pipe 43 is higher to a preset value, the switch valve 70 is controlled to be opened, the driving gas enters the anesthetic agent storage tank 30 via the first pipe 41 and the third pipe 43, and the anesthetic evaporator 100 returns to the normal working state. By providing the pressure sensor 60 and the switch valve 70, the entire system is automatically activated after the completion of the anesthetic agent adding action without additional operations by the operator, which greatly simplifies the operation process, is convenient to use, and improves the user experience.

Referring to FIG. 1, the anesthetic evaporator 100 may further include a pipeline 80 and an evaporation chamber 90 which are in communication with a bottom of the anesthetic agent storage tank 30. A tail end of the pipeline 80 may be provided with a nozzle 82, and the nozzle 82 can be located in the evaporation chamber 90. Under the action of the high-pressure driving gas, the anesthetic agent within the anesthetic agent storage tank 30 may be sprayed out from the nozzle 82 in a mist form and may form an anesthetic agent gas which fills up the evaporation chamber 90. The evaporation chamber 90 may be provided with a gas inlet 91 and a gas outlet 92, and a carrier gas may enter the evaporation chamber 90 from the gas inlet 91, is mixed with the anesthetic agent gas, and is then discharged from the gas outlet 92. The pipeline 80 may also be provided with a control valve 81 to control the on-off between the anesthetic agent storage tank 30 and the evaporation chamber 90.

When the anesthetic agent adding operation is needed for the anesthetic evaporator 100, the action of opening the cover 20 may trigger the cam mechanism to push the valve stem assembly 45 to move, where the valve stem assembly 45 is moved from the first position to the second position, the mechanical pressure relief assembly 40 is switched from the first state to the second state, and the driving gas stops entering the anesthetic agent storage tank 30. Further, the driving gas within the anesthetic agent storage tank 30 is discharged via the third pipe 43 and the first pipe 41, the pressure sensor 60 detects that the pressure within the anesthetic agent storage tank 30 is decreased to a safe range, the switch valve 70 is controlled to be closed, and the operator operates an anesthetic agent adding container 200 to push open the sealed valve 32, so that the anesthetic agent adding container 200 is in communication with the interior of the anesthetic agent storage tank 30, and the anesthetic agent is injected into the anesthetic agent storage tank 30.

After the anesthetic agent adding is completed, the action of the operator of closing the cover 20 may trigger the cam mechanism to push the valve stem assembly 45 to move, where the valve stem assembly 45 is moved from the second position to the first position, the first pipe 41 is in communication with the third pipe 43, and the driving gas enters the third pipe 43 via the first pipe 41. When the pressure sensor 60 detects that the driving gas pressure within the third pipe 43 is higher to a preset value, the switch valve 70 is controlled to be opened, the driving gas enters the anesthetic agent storage tank 30 via the first pipe 41 and the third pipe 43, and the anesthetic evaporator 100 returns to the normal working state.

Figure 3:
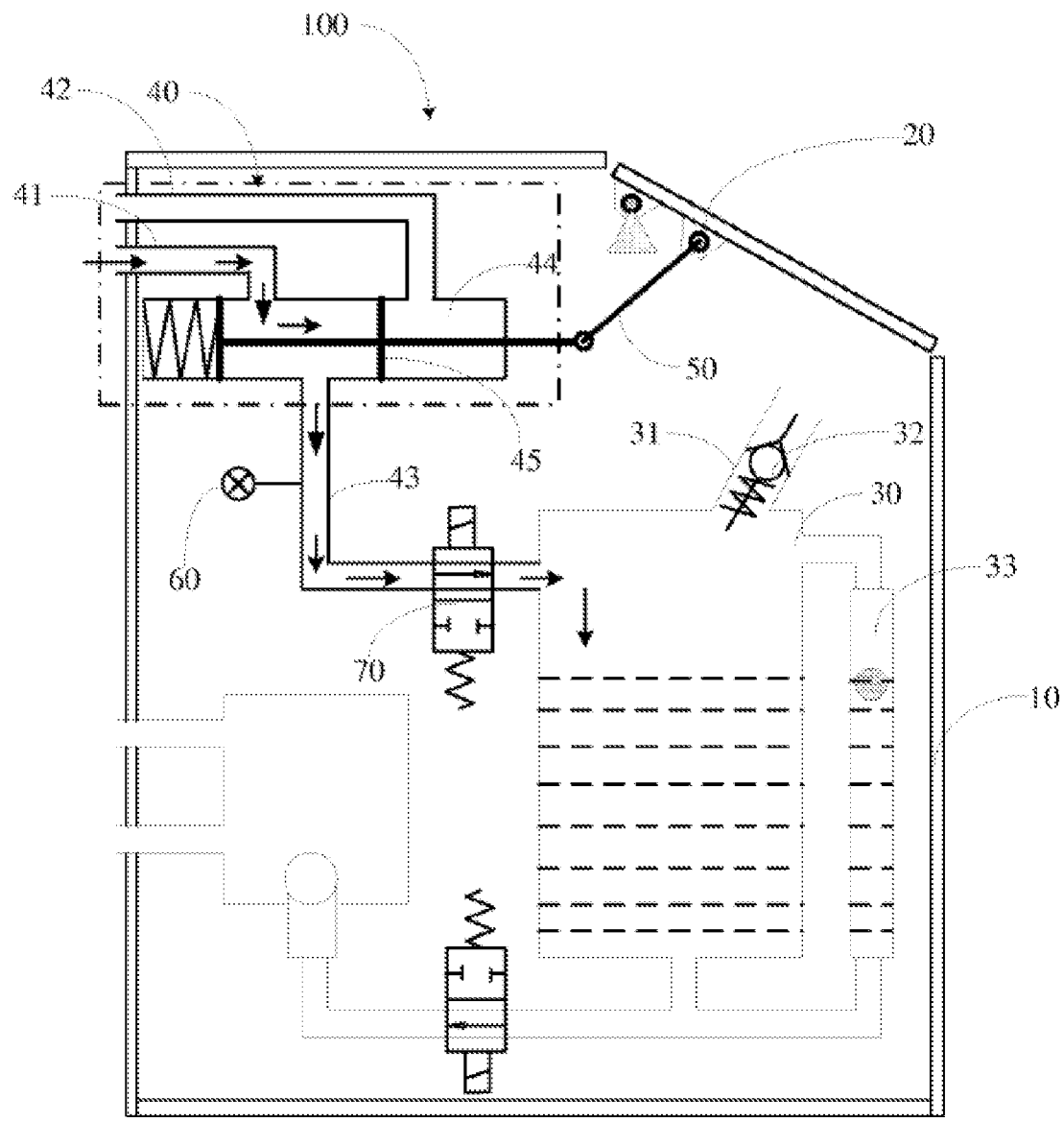
FIG. 3 is a schematic structural diagram of a mechanical pressure relief assembly of an anesthetic evaporator in an embodiment, where the mechanical pressure relief assembly is in a first state.

In a second embodiment, referring to FIG. 3 and FIG. 4, the linkage mechanism 50 can be a connection rod mechanism, a first end of the connection rod mechanism is rotatably connected with the cover 20, and a second end thereof is rotatably connected with the valve stem assembly 45. During the process of opening the cover 20 by rotating around a fixed fulcrum, the connection rod mechanism may be driven to move, which may in turn push the valve stem assembly 45 to move, where the valve stem assembly 45 may be moved from the first position to the second position, the second pipe 42 may become in communication with the third pipe 43, and the high-pressure driving gas within the anesthetic agent storage tank 30 may be discharged out, thereby realizing the pressure relief. Since the connection rod mechanism is connected with the cover 20, the connection rod mechanism may be driven to move during the process of opening the cover 20, so as to realize the mechanical pressure relief to achieve higher safety and reliability of the anesthetic evaporator 100. Other structures are the same as those of the first embodiment, and will not be described again.

When the anesthetic agent adding operation is needed for the anesthetic evaporator 100, the action of opening the cover 20 may trigger the connection rod mechanism to push the valve stem assembly 45 to move, where the valve stem assembly 45 may be moved from the first position to the second position, the mechanical pressure relief assembly 40 may be switched from the first state to the second state, and the driving gas stops entering the anesthetic agent storage tank 30. Further, the driving gas within the anesthetic agent storage tank 30 may be discharged via the third pipe 43 and the first pipe 41, the pressure sensor 60 detects that the pressure within the anesthetic agent storage tank 30 is decreased to the safe range, and the switch valve 70 is controlled to be closed. After the anesthetic agent adding is completed, the action of the operator of closing the cover 20 may trigger the connection rod mechanism to push the valve stem assembly 45 to move, where the valve stem assembly 45 may be moved from the second position to the first position, the first pipe 41 may become in communication with the third pipe 43, and the driving gas can enter the third pipe 43 via the first pipe 41. When the pressure sensor 60 detects that the driving gas pressure within the third pipe 43 is higher to a preset value, the switch valve 70 can be controlled to be opened, the driving gas may enter the anesthetic agent storage tank 30 via the first pipe 41 and the third pipe 43, and the anesthetic evaporator 100 may returns to the normal working state.

Figure 5:
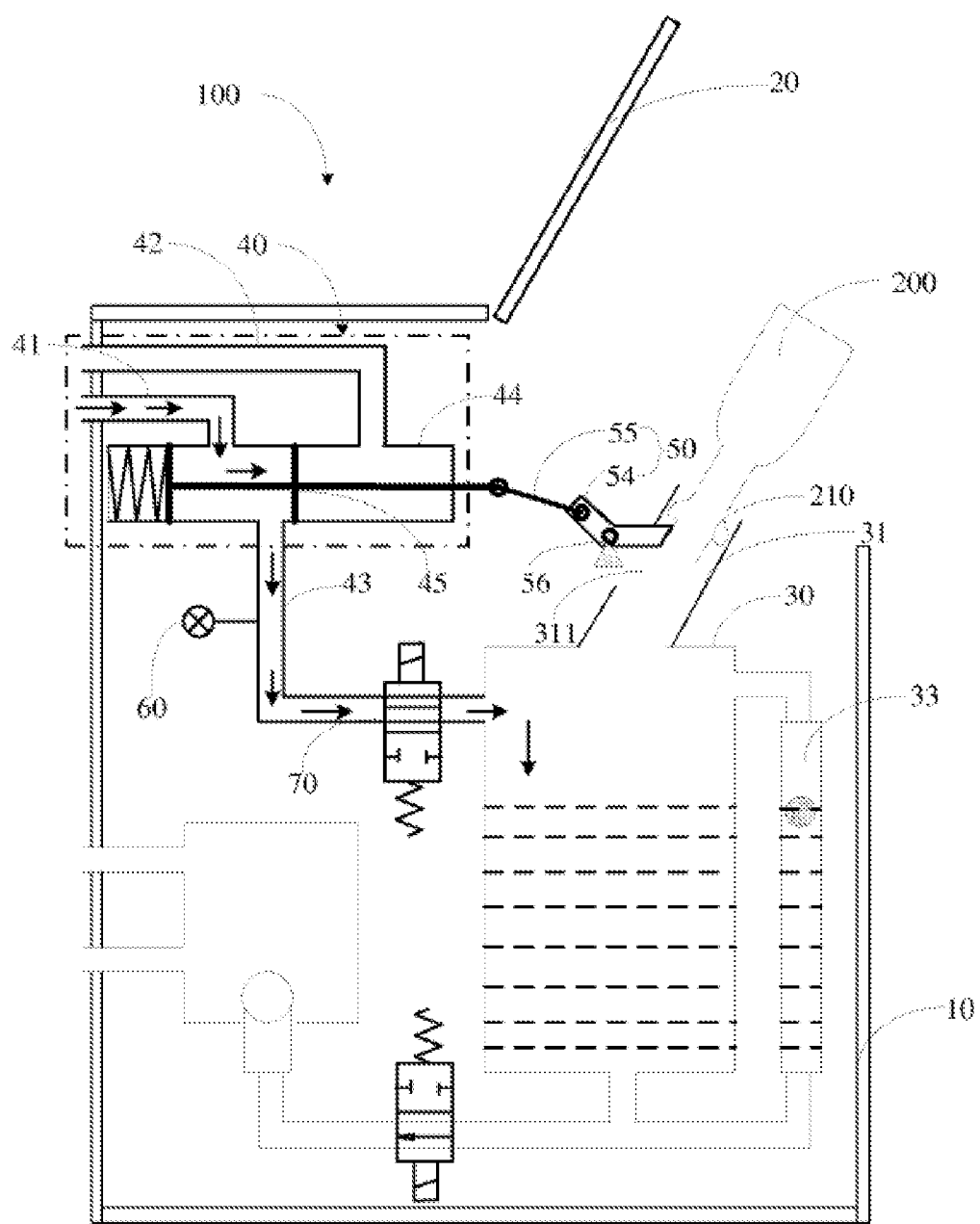
FIG. 5 is a schematic structural diagram of a mechanical pressure relief assembly of an anesthetic evaporator in an embodiment, where the mechanical pressure relief assembly is in a first state.
Figure 6:
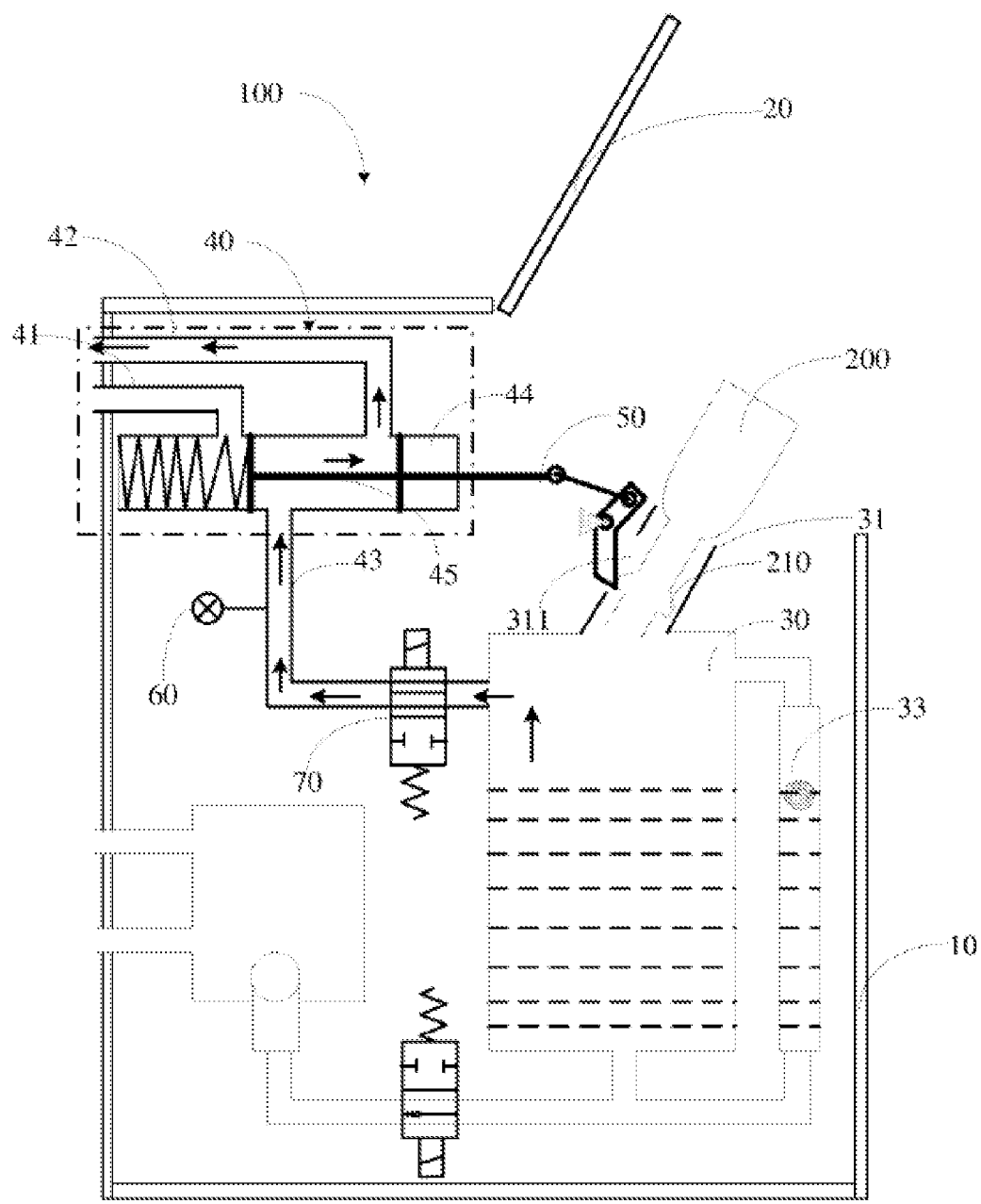
FIG. 6 is a schematic structural diagram of the mechanical pressure relief assembly of the anesthetic evaporator in FIG. 5 in a second state.

In a third embodiment, referring to FIG. 5 and FIG. 6, the linkage mechanism 50 may extend into the anesthetic agent adding barrel 31 on the anesthetic agent storage tank 30. After the operator opens the cover 20, during the process of pushing the anesthetic agent adding container 200 into the anesthetic agent adding barrel 31, the tail end of the linkage mechanism 50 may cooperate with the anesthetic agent adding container 200 and move along with the anesthetic agent adding container 200, thus a part of the structure of the mechanical pressure relief assembly 40 is driven to move, thereby preventing the driving gas from continuing to enter the anesthetic agent storage tank 30. Also, the high-pressure driving gas within the anesthetic agent storage tank 30 is discharged to realize the pressure relief. Other structures are the same as those of the first embodiment, and will not be described again.

Specifically, one end of the linkage mechanism 50 that is remote from the valve stem assembly 45 may pass through a sliding groove 311 on the anesthetic agent adding barrel 31 and enter the interior of the anesthetic agent adding barrel 31. When the anesthetic agent adding container 200 is inserted into the anesthetic agent adding barrel 31, the tail end of the linkage mechanism 50 abuts against a mating portion 210 on the anesthetic agent adding container 200. During the process of pushing in the anesthetic agent adding container 200 along the anesthetic agent adding barrel 31, the linkage mechanism 50 may push the valve stem assembly 45 to move.

The linkage mechanism 50 may include a transmission body 54 and a connection body 55 which two are rotatably connected. The other end of the connection body 55 is rotatably connected with the valve stem assembly 45, a fixed fulcrum 56 is provided in the middle of the transmission body 54, and a tail end of the transmission body 54 may abut against a mating portion 210 of the anesthetic agent adding container 200. During the process pushing in the anesthetic agent adding container 200 along the anesthetic agent adding barrel 31, the transmission body 54 can be pushed to rotate around the fixed fulcrum 56 and drive the connection body 55 to move, thereby pushing the valve stem assembly 45 to move.

When the anesthetic agent adding operation is needed for the anesthetic evaporator 100, the action of pushing the anesthetic agent adding container 200 into the anesthetic agent adding barrel 31 may trigger the linkage mechanism 50 to push the valve stem assembly 45 to move, where the valve stem assembly 45 may be moved from the first position to the second position, the mechanical pressure relief assembly 40 can be switched from the first state to the second state, and the driving gas may stop entering the anesthetic agent storage tank 30. Further, the driving gas within the anesthetic agent storage tank 30 may be discharged via the third pipe 43 and the first pipe 41, the switch valve 70 can be controlled to be closed when the pressure sensor 60 detects that the pressure within the anesthetic agent storage tank 30 is decreased to a safe range, and the operator may operate the anesthetic agent adding container 200 to push open the sealed valve 32, so that the anesthetic agent adding container 200 is in communication with the interior of the anesthetic agent storage tank 30, and the anesthetic agent can be injected into the anesthetic agent storage tank 30. After the anesthetic agent adding is completed, the action of the operator of removing the anesthetic agent adding container 200 from the anesthetic agent adding barrel 31 may trigger the linkage mechanism 50 to push the valve stem assembly 45 to move, where the valve stem assembly 45 may be moved from the second position to the first position, the first pipe 41 may become in communication with the third pipe 43, and the driving gas may enter the third pipe 43 via the first pipe 41. When the pressure sensor 60 detects that the driving gas pressure within the third pipe 43 is higher to a preset value, the switch valve 70 can be controlled to be opened, the driving gas can enter the anesthetic agent storage tank 30 via the first pipe 41 and the third pipe 43, and the anesthetic evaporator 100 may return to the normal working state.

The various technical features of the embodiments described above can be combined in any way. In order to simplify the description, all possible combinations of the various technical features in the above embodiments have not been described. However, any combination of these technical features should be considered to fall with the scope of the disclosure of this description as long as there is no contradiction.

The above-mentioned embodiments merely represent several implementations of the present invention, giving specifics and details thereof, but should not be understood as limiting the scope of the present patent of invention thereby. It should be noted that a person of ordinary skill in the art could also make several variations and improvements without departing from the concept of the present invention, and these variations and improvements would all fall within the scope of protection of the present invention. Therefore, the scope of protection of the present patent of invention shall be in accordance with the appended claims.

The invention claimed is:

1. An anesthetic evaporator, comprising:
a housing;
an anesthetic agent storage tank;
a cover that is movably connected with the housing, the anesthetic agent storage tank being provided with an anesthetic agent adding barrel arranged corresponding to the cover;
a mechanical pressure relief assembly connected with the anesthetic agent storage tank, wherein the mechanical pressure relief assembly is provided with a first state in which a pressure within the anesthetic agent storage tank is maintained and a second state in which a pressure within the anesthetic agent storage tank is released; and
a linkage mechanism, wherein when adding an anesthetic agent, an operation action on the anesthetic evaporator drives the linkage mechanism, and the linkage mechanism drives the mechanical pressure relief assembly to be switched from the first state to the second state, wherein a first end of the linkage mechanism is connected with the cover, a second end of the linkage mechanism is connected with the mechanical pressure relief assembly, and the operation action on the anesthetic evaporator comprises opening the cover,
wherein,
the mechanical pressure relief assembly comprises a main body, a first pipe, a second pipe, a third pipe, and a valve stem assembly, wherein:
a first end of the first pipe is connected with the main body, and a second end of the first pipe is connected with a driving gas source;
a first end of the second pipe is connected with the main body, and a second end of the second pipe is connected with an exhaust gas treatment system;
a first end of the third pipe is connected with the main body, and a second end of the third pipe is in communication with the anesthetic agent storage tank; and
the linkage mechanism is connected with the valve stem assembly.

2. The anesthetic evaporator of claim 1, wherein
when the valve stem assembly is in a first position, the first pipe is in communication with the third pipe, and the mechanical pressure relief assembly is in the first state; and
when adding the anesthetic agent, the operation action is performed on the anesthetic evaporator, the linkage mechanism is driven to push the valve stem assembly to move to a second position, the third pipe becomes in communication with the second pipe, and the mechanical pressure relief assembly is in the second state.

3. The anesthetic evaporator of claim 1, wherein the valve stem assembly comprises a valve stem and an elastic member, a first end of the elastic member is connected with a side wall of the main body, and a second end of the elastic member is connected with the valve stem.

4. The anesthetic evaporator of claim 1, wherein the anesthetic evaporator further comprises a pressure sensor and a switch valve that are provided on the third pipe, and the pressure sensor is located between the switch valve and the main body.

5. The anesthetic evaporator of claim 1, wherein the linkage mechanism is a cam mechanism; and a first end of the cam mechanism is fixedly connected with the cover and a second end of the cam mechanism is slidably connected with the valve stem assembly.

6. The anesthetic evaporator of claim 1, wherein the linkage mechanism is a connection rod mechanism; and a first end of the connection rod mechanism is rotatably connected with the cover, and a second end of the connection rod mechanism is rotatably connected to the valve stem assembly.

7. The anesthetic evaporator of claim 1, wherein the anesthetic evaporator further comprises:
a liquidometer for detecting a liquid level within the anesthetic agent storage tank; or
a sealed valve accommodated in the anesthetic agent adding barrel.

8. The anesthetic evaporator of claim 1, wherein the anesthetic evaporator further comprises a pipeline, a nozzle and an evaporation chamber which are in communication with the anesthetic agent storage tank, wherein a first end of the pipeline is arranged at a bottom of the anesthetic agent storage tank, a second end of the pipeline is connected with the nozzle, and the evaporation chamber is provided with a gas inlet and a gas outlet.

9. An anesthetic evaporator, comprising:
a housing;
an anesthetic agent storage tank;
a cover that is movably connected with the housing, the anesthetic agent storage tank being provided with an anesthetic agent adding barrel arranged corresponding to the cover;
a mechanical pressure relief assembly connected with the anesthetic agent storage tank, wherein the mechanical pressure relief assembly is provided with a first state in which a pressure within the anesthetic agent storage tank is maintained and a second state in which a pressure within the anesthetic agent storage tank is released; and
a linkage mechanism, wherein when adding an anesthetic agent, an operation action on the anesthetic evaporator drives the linkage mechanism, and the linkage mechanism drives the mechanical pressure relief assembly to be switched from the first state to the second state, wherein:
a first end of the linkage mechanism extends into the anesthetic agent adding barrel, and a second end of the linkage mechanism is connected with the mechanical pressure relief assembly; and the operation action on the anesthetic evaporator comprises pushing an anesthetic agent adding container into the anesthetic agent adding barrel; and wherein the mechanical pressure relief assembly comprises a main body, a first pipe, a second pipe, a third pipe, and a valve stem assembly, wherein:
a first end of the first pipe is connected with the main body, and a second end of the first pipe is connected with a driving gas source;
a first end of the second pipe is connected with the main body, and a second end of the second pipe is connected with an exhaust gas treatment system;
a first end of the third pipe is connected with the main body, and a second end of the third pipe is in communication with the anesthetic agent storage tank; and
the linkage mechanism is connected with the valve stem assembly.

10. The anesthetic evaporator of claim 9, wherein
when the valve stem assembly is in a first position, the first pipe is in communication with the third pipe, and the mechanical pressure relief assembly is in the first state; and
when adding the anesthetic agent, the operation action is performed on the anesthetic evaporator, the linkage mechanism is driven to push the valve stem assembly to move to a second position, the third pipe becomes in communication with the second pipe, and the mechanical pressure relief assembly is in the second state.

11. The anesthetic evaporator of claim 9, wherein the valve stem assembly comprises a valve stem and an elastic member, a first end of the elastic member is connected with a side wall of the main body, and a second end of the elastic member is connected with the valve stem.

12. The anesthetic evaporator of claim 9, wherein the anesthetic evaporator further comprises a pressure sensor and a switch valve that are provided on the third pipe, and the pressure sensor is located between the switch valve and the main body.

13. The anesthetic evaporator of claim 9, wherein a side wall of the anesthetic agent adding barrel is provided with a sliding groove, and the anesthetic agent adding container is formed with a mating portion, wherein when the linkage mechanism extends into the anesthetic agent adding barrel from the sliding groove, the mating portion abuts against the first end of the linkage mechanism.

14. The anesthetic evaporator of claim 9, wherein the linkage mechanism comprises a connection body and a transmission body rotatably connected with the connection body, wherein one end of the connection body that is remote from the transmission body is connected with the mechanical pressure relief assembly, and another end of the transmission body extends into the anesthetic agent adding barrel.

15. The anesthetic evaporator of claim 9, wherein the anesthetic evaporator further comprises:

a liquidometer for detecting a liquid level within the anesthetic agent storage tank; or
a sealed valve accommodated in the anesthetic agent adding barrel.

16. The anesthetic evaporator of claim 9, wherein the anesthetic evaporator further comprises a pipeline, a nozzle, and an evaporation chamber which are in communication with the anesthetic agent storage tank, wherein a first end of the pipeline is arranged at a bottom of the anesthetic agent storage tank, a second end of the pipeline is connected with the nozzle, and the evaporation chamber is provided with a gas inlet and a gas outlet.

17. An anesthetic evaporator, comprising:
a housing;
an anesthetic agent storage tank;
a cover that is movably connected with the housing, the anesthetic agent storage tank being provided with an anesthetic agent adding barrel arranged corresponding to the cover;
a mechanical pressure relief assembly connected with the anesthetic agent storage tank, wherein the mechanical pressure relief assembly is provided with a first state in which a pressure within the anesthetic agent storage tank is maintained and a second state in which a pressure within the anesthetic agent storage tank is released; and
a linkage mechanism, wherein when adding an anesthetic agent, an operation action on the anesthetic evaporator drives the linkage mechanism, and the linkage mechanism drives the mechanical pressure relief assembly to be switched from the first state to the second state,
wherein:
the mechanical pressure relief assembly comprises a main body, a first pipe, a second pipe, a third pipe, and a valve stem assembly, wherein
a first end of the first pipe is connected with the main body, and a second end of the first pipe is connected with a driving gas source;
a first end of the second pipe is connected with the main body, and a second end of the second pipe is connected with an exhaust gas treatment system;
a first end of the third pipe is connected with the main body, and a second end of the third pipe is in communication with the anesthetic agent storage tank; and
the linkage mechanism is connected with the valve stem assembly.

18. The anesthetic evaporator of claim 17, wherein a first end of the linkage mechanism is connected with the cover, a second end of the linkage mechanism is connected with the valve stem assembly, and the operation action on the anesthetic evaporator comprises opening the cover.

19. The anesthetic evaporator of claim 17, wherein a first end of the linkage mechanism extends into the anesthetic agent adding barrel, and a second end of the linkage mechanism is connected with the valve stem assembly; and the operation action on the anesthetic evaporator comprises pushing an anesthetic agent adding container into the anesthetic agent adding barrel.

* * * * *